United States Patent [19]
Crossley et al.

[11] Patent Number: 4,666,900
[45] Date of Patent: May 19, 1987

[54] ANTI-ULCER AND ANTI-HYPERSECRETION DIBENZOIMIDAZOTHIAZEPINE DERIVATIVES, COMPOSITIONS, AND METHOD OF USE THEREFOR

[75] Inventors: Roger Crossley, Reading; Peter J. Meade, Maidenhead, both of England

[73] Assignee: John Wyeth & Brother Ltd., Maidenhead, England

[21] Appl. No.: 839,015

[22] Filed: Mar. 12, 1986

[30] Foreign Application Priority Data

Mar. 14, 1985 [GB] United Kingdom ............... 8506657

[51] Int. Cl.[4] ................. A61K 31/38; A61K 31/55; C07D 513/04
[52] U.S. Cl. ................................. 514/211; 540/546
[58] Field of Search ............... 548/324; 514/211; 540/546

[56] References Cited

U.S. PATENT DOCUMENTS 3,932,395 1/1976 Hideg et al. ............... 548/324

FOREIGN PATENT DOCUMENTS 2141429 6/1984 United Kingdom ............ 260/245.6

OTHER PUBLICATIONS

J. Chem. Soc. (C), 1969, 1334–6.
J. Org. Chem., 39(12), 1780–2 (1974).

Primary Examiner—John M. Ford
Assistant Examiner—J. G. Mullins
Attorney, Agent, or Firm—George Tarnowski

[57] ABSTRACT

This invention relates to compounds of formula

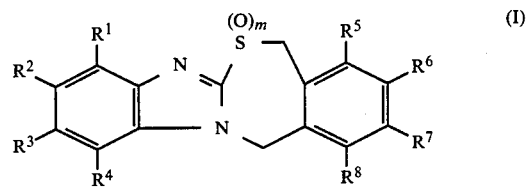

or a pharmaceutically acceptable salt thereof wherein $R^1$, $R^2$, $R^3$, $R^4$ independently represent hydrogen or a substituent selected from lower alkyl, lower alkoxy, halogen, alkanoyl of 2 to 7 carbon atoms, lower alkoxycarbonyl, halolower alkyl, hydroxy, cyano, amino, mono- or diloweralkyl amino, $C_2$–$C_7$ alkanoylamino, carboxy, carboxylower alkyl, hydroxyloweralkyl, carbamoyl, carbamoyloxy, lower alkyl- or aryl-carbonyl, (lower alkoxy)-lower alkoxy, phenyl or a phenyl group itself optionally substituted by a substituent as hereinbefore defined excepting phenyl, or an adjacent pair of $R^{1-4}$ together with the carbon atoms to which they are attached complete a six membered unsaturated carbocyclic or nitrogen containing heterocyclic ring, optionally substituted by one or more of the substituents listed above for $R^1$; m represents 0 or 1; and $R^5$, $R^6$, $R^7$ and $R^8$ independently represent hydrogen or a substituent selected from lower alkyl, lower alkoxy, halogen, alkanoyloxy of 2 to 7 carbon atoms, lower alkoxycarbonyl and hydroxy and the term 'lower' means a group containing 1 to 6 carbon atoms; which compounds possess antisecretory activity and are useful for the treatment of hypersecretion or ulcers.

9 Claims, No Drawings

ANTI-ULCER AND ANTI-HYPERSECRETION DIBENZOIMIDAZOTHIAZEPINE DERIVATIVES, COMPOSITIONS, AND METHOD OF USE THEREFOR

This invention relates to heterocyclic compounds, more particularly to dibenzoimidazothiazepines, to processes for preparing them and to pharmaceutical compositions containing them.

In UK Patent Publication No. 2141429 there are described a series of tricyclic thiazolo- and thiazinobenzimidazoles possessing pharmaceutical activity, in particular antiulcer and antisecretory activity. The thiazolo and thiazino-benzimidazoles are useful as antiulcer agents or for the treatment of gastric hypersecretion and particularly for the treatment of peptic ulcer disease.

We have now found a novel series of tetracyclic dibenz[d,h]imidazo thiazepines possessing pharmaceutical activity in particular antisecretory activity and hence are also useful for the treatment of gastric hypersecretion and as antiulcer agents especially in the treatment of peptic ulcers.

Accordingly this invention provides compounds of formula:

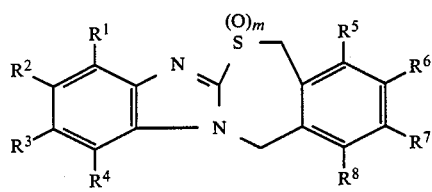
(I)

or a pharmaceutically acceptable salt thereof wherein $R^1$, $R^2$, $R^3$, $R^4$ independently represent hydrogen or a substituent selected from lower alkyl, lower alkoxy, halogen, alkanoyl of 2 to 7 carbon atoms, lower alkoxycarbonyl, halolower alkyl, hydroxy, cyano, amino, mono- or diloweralkyl amino, $C_2$-$C_7$ alkanoylamino, carboxy, carboxylower alkyl, hydroxyloweralkyl, carbamoyl, carbamoyloxy, lower alkyl- or aryl-carbonyl, (lower alkoxy)-lower alkoxy, phenyl or a phenyl group itself optionally substituted by a substituent as hereinbefore defined excepting phenyl, or an adjacent pair of $R^{1-4}$ together with the carbon atoms to which they are attached complete a six membered unsaturated carbocyclic or nitrogen containing heterocyclic ring, optionally substituted by one or more of the substituents listed above for $R^1$, m represents 0 or 1; and $R^5$, $R^6$, $R^7$ and $R^8$ independently represent hydrogen or a substituent selected from lower alkyl, lower alkoxy, halogen, alkanoyloxy of 2 to 7 carbon atoms, lower alkoxycarbonyl and hydroxy.

The term "lower" as used herein to qualify a group means such a group contains 1 to 6 carbon atoms. Examples of any one of $R^{1-4}$ when substituents are methyl, ethyl, propyl, butyl, isopropyl, methoxy, ethoxy, propoxy, isopropoxy, butoxy, chlorine, bromine, fluorine, acetoxy, propionyloxy, butyryloxy, methoxycarbonyl, ethoxycarbonyl, propoxycarbonyl, trifluoromethyl, hydroxy, cyano, amino, methylamino, dimethylamino, ethylamino, acetylamino,carboxy, carboxymethyl, hydroxymethyl, hydroxyethyl, carbamoyl, carbamoyloxy, acetyl, benzoyl or phenyl.

When any adjacent pair of $R^1$, $R^2$, $R^3$ and $R^4$ complete a fused ring examples of the additional rings are benzo- and pyrido-fused rings. For example when $R^2$ and $R^3$ form a benzo fused ring the compound of formula I has the general formula

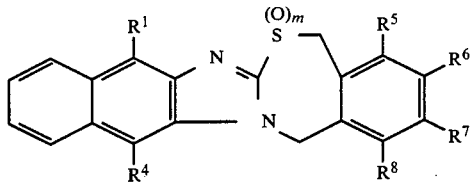

Examples of any one of $R^{5-8}$ when substituted are methyl, ethyl, propyl, fluorine, methoxy, ethoxy, chlorine, bromine, acetoxy, propionyloxy, methoxycarbonyl, ethoxycarbonyl and hydroxy.

Preferred compounds of this invention are:
8,13-Dihydrodibenzo[d,h]imidazo[2,1-b][1,3]thiazepine,
8,13-dihydro-4,5-dimethyldibenzo[d,h]imidazo[2,1-b][1,3]thiazepine.
8,13-dihydro-4-methoxydibenzo[d,h]imidazo[2,1-b][1,3]thiazepine and
8,13-dihydro-5-methoxydibenzo[d,h]imidazo[2,1-b][1,3]-thiazepine.

Examples of acid addition salts of the compounds of the invention are those formed from inorganic and organic acids, in particular pharmaceutically acceptable acid addition salts such as the hydrochloride, hydrobromide, hydroiodide, sulphate, nitrate, phosphate, sulphonate (such as the methanesulphonate and p-toluenesulphonate) acetate, maleate, citrate, fumarate, tartrate, malonate and formate. The salts also include quaternary ammonium salts such as those formed from alkyl or aralkyl halides.

Compounds of formula I were tested for anti-secretory activity by their ability to inhibit the effect of one or two secretagogues on isolated gastric glands.

Potential inhibitors of the highly specific proton transporting enzyme $H^+/K^+$ ATPase were evaluated by a technique involving the measurement of aminopyrine accumulation in rabbit isolated gastric glands. Aminopyrine accumulates in acid-secreting cells; therefore, uptake of aminopyrine is increased by secretagogues and an inhibitor of acid secretion will reduce the response to one or more secretagogues depending upon its site of action. Compounds which reduce the response to dibutyryl cyclic adenosine monophosphate (DBcAMP) stimulation are assumed to have an intracellular site of action, and those which reduce the response to both DBcAMP and high potassium ion concentration ($K^+$) are thought to have an intracellular site of action at the secretory surface of the parietal cell, involving the highly specific proton-transporting enzyme, $H^+/K^+$ ATPase.

The following procedure is used:
Rabbit glands are isolated from gastric mucosa from the corpus region of the stomach by a method based on one described by Berglindh T., Obrink K. J., Acta Physiol. Scand. 96, 150–159 (1976). Measurement of aminopyrine uptake is carried out using a procedure based on the method described by Berglindh T., Hellander H. F., Obrink K. J. (ibid. 97 401–414, 1976).

Compounds are tested at a concentration of $10^{-4}M$, for their ability to inhibit C-aminopyrine uptake in gastric glands, stimulated by DBcAMP and high $K^+$ respectively. Results are expressed as the % inhibition of the maximum response to the secretagogue induced by the test compound.

In the above test the following representative compounds of formula I gave the results shown:

| Compound | % Inhibition to DBcAMP | stimulation by: k+ |
|---|---|---|
| 8,13-Dihydrodibenzo[d,h]-imidazo[2,1-b][1,3]-thiazepine | 32% at $10^{-4}$M | 94% at $10^{-4}$M |
| 8,13-Dihydro-4,5-dimethyl-dibenzo[d,h]imidazo[2,1-b]-[1,3]thiazepine | ns at $10^{-4}$M | 80% at $10^{-4}$M |
| A 60:40 mixture of 8,13-Dihydro-4-methoxydibenzo-[d,h]imidazo[2,1-b][1,3]thiazepine + 8,13-Dihydro-5-methoxydibenzo-[d,h]imidazo[2,1-b][1,3]thiazepine | ns at $10^{-6}$M | 108% at $10^{-4}$M |
| 8,13-Dihydrodibenzo[d,h]imidazo-[2,1-b][1,3]thiazepine-1-oxide | 31% at $10^{-4}$M | ns at $10^{-4}$M | ns = not significant

This invention also provides processes for preparing the compounds of formula I.

A first process for preparing the compounds of formula I comprises cyclising a compound of formula

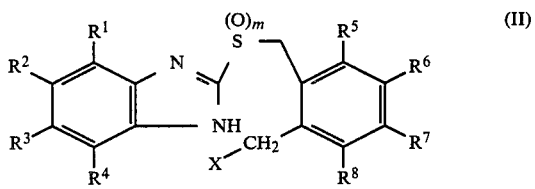

wherein $R^{1-8}$ and m are as defined above and X represents OH or a leaving group such as halogen or an organic sulphonyloxy group such as an alkyl-, aryl- or aralkylsulphonyloxy group (e.g. tosyloxy, mesyloxy). The cyclisation is conveniently carried out in an inert solvent if desired under basic conditions (e.g. triethylamine, potassium carbonate) with heating if required. When X is OH the cyclisation may be carried out in acidic solvent such as acetic anhydride.

Compounds of formula II may be prepared by reacting an appropriate 2-chlorobenzimidazole with a compound of formula

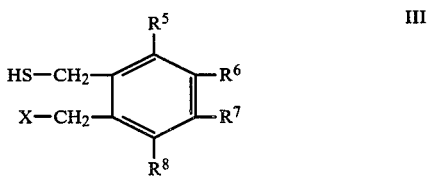

wherein X and $R^{5-8}$ are as hereinbefore defined and if desired oxidising the product e.g. using a peroxyorganic acid such as a peroxybenzoic acid.

Compounds of formula II wherein m=0 may also be prepared by coupling an alkali metal salt of 2-mercaptobenzimidazole, e.g. the sodium salt with a compound of formula

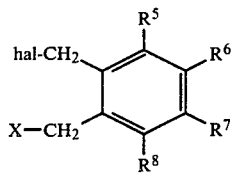

where X and $R^{5-8}$ are as hereinbefore defined and hal is a halogen such as chlorine.

A second process for preparing compounds of formula I wherein m is 0 comprises cyclising a compound of formula

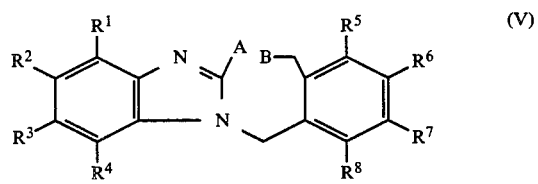

wherein $R^{1-8}$ are as hereinbefore defined and one of A and B is —SH, the other is a leaving group such as radicals mentioned above providing that when A is —SH then B may also represent OH. When either of A and B is a leaving group the cyclisation is conveniently carried out by heating if desired in the presence of base (e.g. triethylamine, potassium carbonate etc.). When B is OH the cyclisation may be carried out in the presence of a strong acid e.g. HCl or polyphosphoric acid.

Compounds of formula V where B is OH and A is SH may be prepared by reacting an appropriate 2-chlorobenzimidazole with a compound of formula

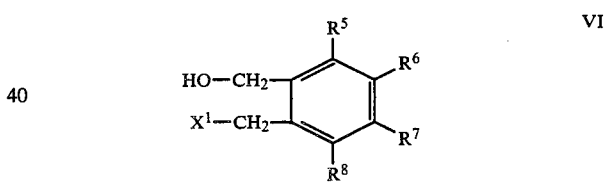

to give a compound of formula

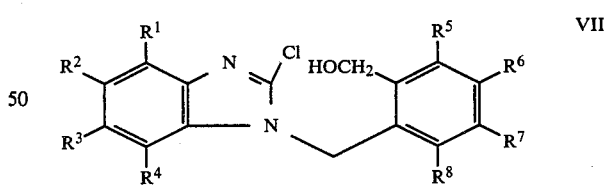

in which formulae $R^{1-8}$, are as hereinbefore defined and $X^1$ is a leaving group, e.g. halogen and then reacting the compound of formula VII with thiourea to give a 2-isothiouronium compound. The product is treated with an alkali metal hydroxide or ammonium hydroxide under mild conditions, e.g. without heating.

Compounds of formula V wherein A is SH and B is a leaving group may be prepared from the corresponding compounds of formula VI wherein B is OH by known methods e.g. halogenation, sulphonylation to convert OH to a leaving group.

Compounds of formula V wherein A is a leaving group such as halogen and B is SH may be prepared by building up the molecule from appropriate starting materials wherein the —SH is protected by a thiol protecting group and removing the protecting group as the final step.

Compounds of formula I wherein m is 0 may also be prepared by a process which comprises reducing a compound of formula

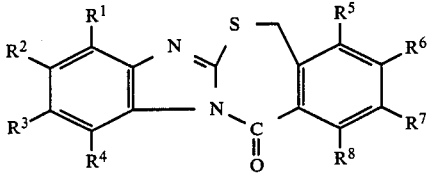

wherein $R^{1-8}$, are as hereinbefore defined.

This reduction may be carried out using a metal hydride, e.g. lithium aluminium hydride. The compounds of formula VIII may be prepared by cyclising a corresponding compound of formula IX

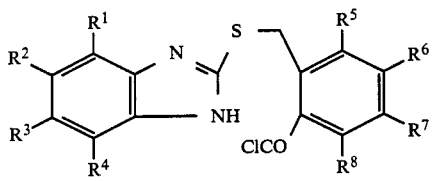

wherein $R^{1-8}$ are as defined above.

Compounds of formula IX may be prepared by reacting the appropriate 2-mercaptobenzimidazole with a halo-acid of formula

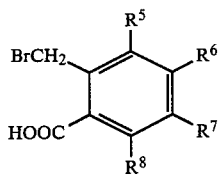

($R^{5-8}$ as defined herein) and converting the acid to the acid chloride.

In yet a further process the compounds of formula I wherein m is 0 may be prepared by reacting a compound of formula

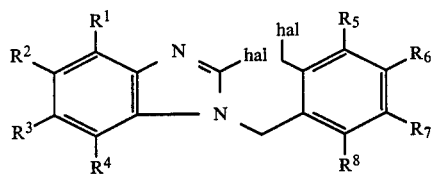

wherein hal and $R^{1-8}$ are as hereinbefore defined with
 (i) an alkali metal sulphide or hydrosulphide,
 (ii) ammonium sulphide or polysulphide or
 (iii) H$_2$S in the presence of a tertiary amine.

In a preferred process for preparing the compounds of formula I the compounds of formula II wherein m is 0 are prepared and cyclised without isolation in a single step process by reacting an appropriate 2-mercaptobenzimidazole of formula

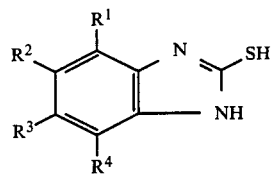

wherein $R^1$, $R^2$, $R^3$ and $R^4$ are as defined above with a compound of formula

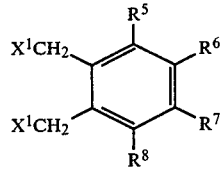

wherein $R^{5-8}$ are as hereinbefore defined, the $X^1$ groups being the same or different halogens. This reaction is conveniently carried out by heating in a suitable solvent, e.g. dimethylformamide, if desired in the presence of base.

It should be noted that due to tautomerism certain ring substituted 2-mercaptobenzimidazole starting materials are mixtures and hence mixtures of final products are obtained. For example 2-mercapto-5-methylbenzimidazole is tautomeric with 2-mercapto-6-methylbenzimidazole and the final product will be a mixture of compounds where $R^2$ or $R^3$ is methyl.

Compounds of formula I wherein m is 0 and 1 may be interconverted. For example when m is 0 the compounds may be oxidised to the corresponding oxides of formula I wherein m is 1 by treatment with suitable oxidising agents e.g. hydrogen peroxide, sodium periodate, peroxy acids such as peroxybenzoic acids and peroxyalkanoic acids. When m is 1 the compound of formula I may be reduced to the corresponding compound where m is 0 using a reducing agent such as a metal or boron hydride, e.g. BHCl$_2$. Accordingly compounds of formula I are intermediates for other compounds of formula I.

The compounds of formula I which are sulphoxides possess an asymmetric centre and hence optical isomers and mixtures thereof are possible. All such isomers and mixtures thereof are included within the scope of this invention. Where any reaction process produces mixtures of such isomers standard resolution techniques may be applied to separate a specific isomer.

In any of the aforementioned reactions compounds of formula I may be isolated in free base form or as acid addition salts as desired. Quaternary ammonium salts may be prepared by reaction with an appropriate halide.

The invention further provides a compound of formula (I) or a pharmaceutically acceptable acid addition salt for use as a pharmaceutical.

The invention also provides a pharmaceutical composition comprising a compound of general formula (I) or a pharmaceutically acceptable acid addition salt thereof in association with a pharmaceutically acceptable carrier. Any suitable carrier known in the art can be used to prepare the pharmaceutical composition. In such a composition, the carrier is generally a solid or liquid or a mixture of a solid and a liquid.

Solid form compositions include powders, granules, tablets, capsules (e.g. hard and soft gelatine capsules), suppositories and pessaries. A solid carrier can be, for example, one or more substances which may also act as flavouring agents, lubricants, solubilisers, suspending agents, fillers, glidants, compression aides, binders or tablet-disintegrating agents; it can also be an encapsulating material. In powders the carrier is a finely divided active ingredient. In tablets the active ingredient is mixed with a carrier having the necessary compression properties in suitable proportion and compacted in the shape and size desired. The powders and tablets preferably contain up to 99%, e.g. from 0.03 to 99%, preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxylmethyl cellulose, polyvinylpyrrolidine, low melting waxes and ion exchange resins.

The term "composition" is intended to include the formulation of an active ingredient with encapsulating material as carrier to give a capsule in which the active ingredient (with or without other carriers) is surrounded by the carrier, which is thus in association with it. Similarly cachets are included.

Liquid form compositions include, for example, solutions, suspensions, emulsions, syrups, elixirs and pressurised compositions. The active ingredient, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilisers, emulsifiers, buffers, preservatives, sweeteners, flavouring agents, suspending agents, thickening agents, colours, viscosity regulators, stabilisers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycerol and glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. When the compound is orally active it can be administered orally either in liquid or solid composition form.

Preferably the pharmaceutical composition is in unit dosage form, e.g. as tablets or capsules. In such form, the composition is sub-divided in unit doses containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form. The quantity of the active ingredient in unit dose of composition may be varied or adjusted from 0.5 mg or less to 750 mg or more, according to the particular need and the activity of the active ingredient. The invention also includes the compounds in the absence of the carrier where the compounds are in unit dosage form.

The anti-ulcer compositions of the invention will be administered orally in either liquid or solid composition form. These compositions may include one or more antacid ingredients, e.g. aluminium hydroxide, magnesium hydroxide or bismuth carbonate, aluminium glycinate, calcium carbonate, magnesium trisilicate, sodium bicarbonate or the alumina gel described in British Specification No. 1,284,394.

In another aspect the invention provides as an anti-ulcer agent a compound of formula I or a pharmaceutically acceptable salt thereof as defined above.

Based on the isolated tissues experiments detailed hereinabove the dosage range for the treatment of humans using a compound of formula I will be in the range from about 5 mg to about 1000 mg per day depending on the activity of the compound and the degree of inhibition desired.

The following Examples illustrate the invention:

EXAMPLE 1

8,13-Dihydrodibenzo[d,h]imidazo[2,1-b][1,3]thiazepine $\alpha,\alpha'$-Dibromo-o-xylene (39.3 g) was added to 2-mercaptobenzimidazole (25 g) in dimethylformamide (200 ml) and the mixture was stirred at ambient temperature for 18 hours and was then heated at 100° C. for 5 hours. The product was removed by filtration and was recrystallised from methanol/ethyl acetate four times to give the title compound as the hydrobromide ¼ hydrate salt, (1.3 g) mp 265.5°–7° C. decomp.

Analysis Found: C, 53.6; H, 3.85; N, 8.4; $C_{15}H_{12}N_2S.HBr.\frac{1}{4}H_2O$ requires C, 53.3; H, 3.9; N, 8.3%.

EXAMPLE 2

8,13-Dihydro-4,5-dimethyldibenzo[d,h]imidazo[2,1-b][1,3]thiazepine 5,6-Dimethyl-2-mercaptobenzimidazole (1.7 g) was added to $\alpha,\alpha'$-dibromo-o-xylene (2.7 g) in ethanol (100 ml) and the mixture was heated at reflux for 6 hours.

The solvent was removed under reduced pressure and the residue washed with 2N HCl. The solid obtained was suspended in saturated sodium carbonate solution and was removed by filtration. The residue was suspended in chloroform and filtered. The organic layer was dried (MgSO₄) and evaporated. The residue was recrystallised twice from ethanol to give the title compound 0.46 g, mp. 228°–230° C.

Analysis Found: C, 72.6; H, 5.8; N, 9.7; $C_{17}H_{16}N_2S$ requires: C, 72.8; H, 5.75; N, 10.0%.

EXAMPLE 3

8,13-Dihydro-4-methoxydibenzo[d,h]imidazo[2,1-b][1,3]thiazepine and 8,13-Dihydro-5-methoxydibenzo[d,h]imidazo[2,1-b][1,3]thiazepine 5-Methoxy-2-mercaptobenzimidazole (3.6 g) was added to $\alpha,\alpha'$-dibromo-o-xylene (5.3 g) in ethanol (100 ml) and the mixture was heated at reflux 4 hours.

The reaction mixture was allowed to cool and was filtered. The filtrates were evaporated under reduced pressure and the residue was purified by chromatography on alumina using dichloromethane as eluent. The solvent was removed under reduced pressure and the residue was crystallised using ether. The product was isolated by filtration to give a 60:40 mixture respectively of the title 4- and 5-methoxy compounds, 0.3 g mp. 144°–146° C.

Analysis Found: C, 68.0; H, 5.0; N, 9.6; $C_{16}H_{14}N_2OS$ requires: C, 68.0; H, 5.0; N, 9.95%.

EXAMPLE 4

4,5-Dichloro-8,13-dihydrodibenzo[d,h]imidazo[2,1-b][1,3]thiazepine 4,5-Dichloro-2-mercaptobenzimidazole (2 g) was added to α,α'-dibromo-o-xylene (2.7 g) in ethanol (100 ml) and was heated at reflux for 6 hours. The solvent was removed under reduced pressure and the residue was suspended in 2N HCl. The aqueous mixture was filtered and the material obtained was washed with water, saturated $Na_2CO_3$ solution and then again with water. The product was dried under vacuum and was recrystallised from ethanol to give the title compound (1.2 g) mp 243.5°–245° C.

Analysis Found: C, 56.2; H, 3.0; N, 8.6; $C_{15}H_{10}Cl_2N_2S$ requires C, 56.1; H, 3.1; N, 8.7%.

EXAMPLE 5

8,13-Dihydrodibenz[d,h]imidazo[2,1-b][1,3]thiazepine-1-oxide 8,13-Dihydrodibenzo[d,h]imidazo[2,1-b][1,3]thiazepine, free base, (1.8 g) was dissolved in ethyl acetate and cooled to −30° C. m-Chloroperoxybenzoic acid (1.2 g) was added as a solid and the mixture allowed to warm over 1 hour to −15° C. when a saturated solution of sodium carbonate (5 ml) was added. The mixture was filtered and dried ($MgSO_4$) and the solvent removed to give a white solid, this was extracted with ethyl acetate (15 ml). The ethyl acetate soluble material was purified by chromatography on Fluorisil using ethyl acetate as eluent to give the title compound as the ¼ hydrate, (350 mg), mp. 210.5°–212° C. decomp.

Analysis Found: C, 65.7; H, 4.4; N, 9.9; $C_{15}H_{12}N_2OS \cdot \tfrac{1}{4}H_2O$ requires C, 66.0; H, 4.6; N, 10.3%.

EXAMPLE 6-17

Using a procedure analogous to Example 1 the following compounds of formula I may be prepared according to the reaction scheme

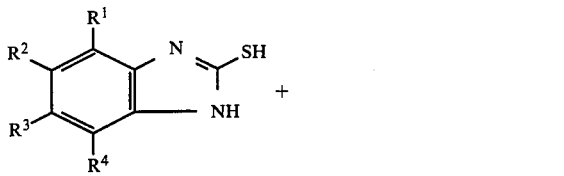

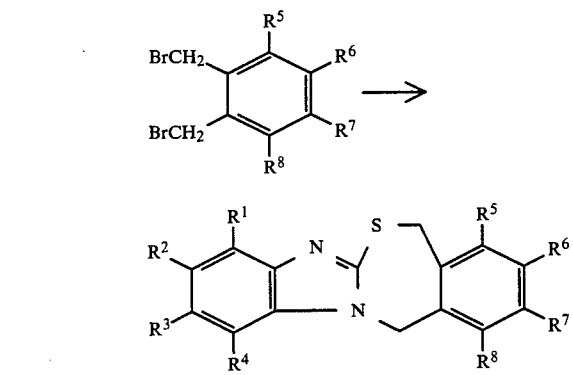

| $R^1$ | $R^2$ | $R^3$ | $R^4$ | $R^5$ | $R^6$ | $R^7$ | $R^8$ |
|---|---|---|---|---|---|---|---|
| H | H | H | H | H | H | Cl | H |
| H | H | H | H | H | Cl | H | H |
| H | Me | Me | H | H | H | Me | H |
| H | Me | Me | H | H | Me | H | H |
| H | H | H | H | H | H | MeO | H |
| H | H | H | H | H | MeO | H | H |
| H | H | H | H | H | H | $CH_3CO$— | H |
| H | H | H | H | H | $CH_3CO$— | H | H |
| H | H | H | H | H | $CH_3OCO$ | H | H |
| H | H | H | H | H | H | $CH_3OCO$— | H |
| H | $CH_3OCO$— | $CH_3OCO$— | H | H | H | H | H |
| H | MeO | MeO | H | H | H | H | H |

We claim:
1. A compound of formula:

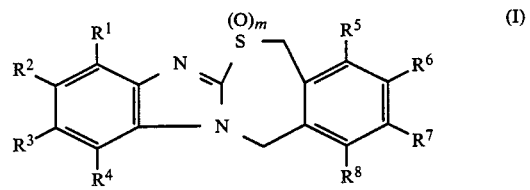

or a pharmaceutically acceptable salt thereof wherein $R^1$, $R^2$, $R^3$, $R^4$ independently represent hydrogen or a substituent selected from lower alkyl, lower alkoxy, halogen, alkanoyloxy of 2 to 7 carbon atoms, lower alkoxycarbonyl, halolower alkyl, hydroxy, cyano, amino, mono- or di-loweralkyl amino, $C_2$-$C_7$ alkanoylamino, carboxy, carboxylower alkyl, hydroxyloweralkyl, carbamoyl, carbamoyloxy, lower alkyl- or arylcarbonyl, (lower alkoxy)-lower alkyl, phenyl and a phenyl itself optionally substituted by a substituent as hereinbefore defined excepting phenyl; m represents 0 or 1; and $R^5$, $R^6$, $R^7$ and $R^8$ independently represent hydrogen or a substituent selected from lower alkyl, lower alkoxy, halogen, alkanoyloxy of 2 to 7 carbon atoms, lower alkoxycarbonyl and hydroxy and the term 'lower' means a group containing 1 to 6 carbon atoms.

2. A compound as claimed in claim 1 wherein any one of $R^1$, $R^2$, $R^3$ and $R^4$ is hydrogen, methyl, ethyl, propyl, butyl, isopropyl, methoxy, ethoxy, propoxy, isopropoxy, butoxy, chlorine, bromine, fluorine, acetoxy, propionyloxy, butyryloxy, methoxycarbonyl, ethoxycarbonyl, propoxycarbonyl, $CF_3-$, $HO-$, $NH_2-$, $MeNH-$, $Me_2N-$, $EtNH-$, cyano acetylamino, carboxy, carboxymethyl, hydroxymethyl, hydroxyethyl, carbamoyl, carbamoyloxy, acetyl, benzoyl or phenyl.

3. A compound as claimed in claim 1 wherein any one of $R^5$, $R^6$, $R^7$ and $R^8$ is methyl, ethyl, propyl, fluorine, chlorine, bromine, methoxy, ethoxy, acetoxy, propionyloxy, methoxycarbonyl, ethoxycarbonyl or hydroxy.

4. A compound as claimed in claim 1 which is 8,13-dihydrodibenzo[d,h]imidazo[2,1-b][1,3]thiazepine or a pharmaceutically acceptable salt thereof.

5. A compound as claimed in claim 1 which is 8,13-dihydro-4,5-dimethyldibenzo[d,h]imidazo[2,1-b][1,3]thiazepine or a pharmaceutically acceptable salt thereof.

6. A compound as claimed in claim 1 which is 8,13-dihydro-4-methoxydibenzo[d,h]imidazo[2,1-b][1,3]thiazepine or a pharmaceutically acceptable salt thereof.

7. A compound as claimed in claim 1 which is 8,13-dihydro-5-methoxydibenzo[d,h]imidazo[2,1-b][1,3]thiazepine or a pharmaceutically acceptable salt thereof.

8. A pharmaceutical composition for treating ulcers or hypersecretion which comprises a therapeutically effective amount of a compound of formula

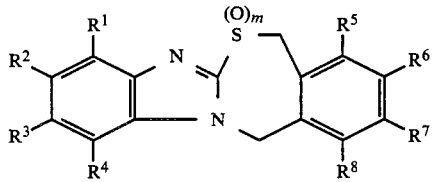

or a pharmaceutically acceptable salt thereof, wherein $R^1$, $R^2$, $R^3$, $R^4$ independently represent hydrogen or a substituent selected from lower alkyl, lower alkoxy, halogen, alkanoyloxy of 2 to 7 carbon atoms, lower alkoxycarbonyl, halolower alkyl, hydroxy, cyano, amino, mono- or di-loweralkyl amino, $C_2-C_7$ alkanoylamino, carboxy, carboxylower alkyl, hydroxyloweralkyl, carbamoyl, carbamoyloxy, lower alkyl- or arylcarbonyl, (lower alkoxy)-lower alkoxy, phenyl and phenyl itself optionally substituted by a substituent as hereinbefore defined excepting phenyl; m represents 0 or 1; and $R^5$, $R^6$, $R^7$ and $R^8$ independently represent hydrogen or a substituent selected from lower alkyl, lower alkoxy, halogen, alkanoyloxy of 2 to 7 carbon atoms, lower alkoxycarbonyl and hydroxy and the term 'lower' means a group containing 1 to 6 carbon atoms, and a pharmaceutically acceptable carrier.

9. A method of treating ulcers or hypersecretion in a mammal which method comprises administering to said mammal in need of such treatment an effective amount of a compound of formula

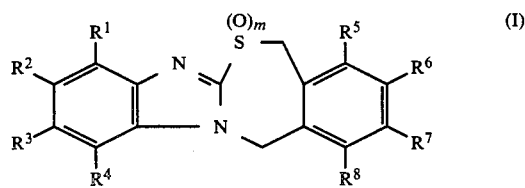

or a pharmaceutically acceptable salt thereof wherein $R^1$, $R^2$, $R^3$, $R^4$ independently represent hydrogen or a substituent selected from lower alkyl, lower alkoxy, halogen, alkanoyloxy of 2 to 7 carbon atoms, lower alkoxycarbonyl, halolower alkyl, hydroxy, cyano, amino, mono- or di-loweralkyl amino, $C_2-C_7$ alkanoylamino, carboxy, carboxylower alkyl, hydroxyloweralkyl, carbamoyl, carbamoyloxy, lower alkyl- or arylcarbonyl, (lower alkoxy)-lower alkoxy, phenyl and phenyl itself optionally substituted by a substituent as hereinbefore defined excepting phenyl; m represents 0 or 1; and $R^5$, $R^6$, $R^7$ and $R^8$ independently represent hydrogen or a substituent selected from lower alkyl, lower alkoxy, halogen, alkanoyloxy of 2 to 7 carbon atoms, lower alkoxycarbonyl and hydroxy and the term 'lower' means a group containing 1 to 6 carbon atoms.

* * * * *